United States Patent
Prisco et al.

(10) Patent No.: US 9,339,342 B2
(45) Date of Patent: May 17, 2016

(54) INSTRUMENT INTERFACE

(75) Inventors: Giuseppe Maria Prisco, Mountain View, CA (US); Theodore W. Rogers, Alameda, CA (US); John Ryan Steger, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 423 days.

(21) Appl. No.: 13/360,395

(22) Filed: Jan. 27, 2012

(65) Prior Publication Data

US 2012/0289973 A1  Nov. 15, 2012
US 2013/0331857 A9  Dec. 12, 2013

Related U.S. Application Data

(63) Continuation-in-part of application No. 12/286,644, filed on Sep. 30, 2008.

(60) Provisional application No. 61/485,702, filed on May 13, 2011.

(51) Int. Cl.
*A61B 17/00* (2006.01)
*A61B 19/00* (2006.01)

(52) U.S. Cl.
CPC ... *A61B 19/2203* (2013.01); *A61B 2017/00477* (2013.01); *A61B 2019/2242* (2013.01)

(58) Field of Classification Search
CPC .... A61B 19/20; A61B 19/22; A61B 19/2203; A61B 2019/2242; A61B 17/00; A61B 17/00234; A61B 2017/0084; A61B 2017/00845

USPC ......... 606/1, 130; 128/898; 901/2, 11, 14, 19, 901/30
See application file for complete search history.

(56) References Cited

U.S. PATENT DOCUMENTS

| | | | | |
|---|---|---|---|---|
| 4,117,359 A | * | 9/1978 | Wehde | 310/67 R |
| 4,259,876 A | | 4/1981 | Belyanin et al. | |
| 4,281,447 A | * | 8/1981 | Miller et al. | 279/156 |
| 4,283,165 A | | 8/1981 | Vertut | |
| 6,132,368 A | | 10/2000 | Cooper | |

(Continued)

FOREIGN PATENT DOCUMENTS

| | | |
|---|---|---|
| CN | 2626684 Y | 7/2004 |
| CN | 102014759 A | 4/2011 |

(Continued)

OTHER PUBLICATIONS

International Search Report and Written Opinion for Application No. PCT/US2012/037269, mailed on Sep. 19, 2012, 10 pages.

(Continued)

*Primary Examiner* — Ahmed Farah

(57) ABSTRACT

A mechanical interface for a robotic medical instrument permits engagement of the instrument and a drive system without causing movement of an actuated portion of the instrument. An instrument interface can include a symmetrical, tapered or cylindrical projection on one of a medical instrument or a drive system and a complementary bore in the other of the drive system or the medical instrument. Symmetry of the projection and the bore allows the projection to be compression fit to the bore regardless of the rotation angle of the drive system relative to the medical instrument.

33 Claims, 4 Drawing Sheets

(56) References Cited

U.S. PATENT DOCUMENTS

| | | | |
|---|---|---|---|
| 6,139,245 A | 10/2000 | Hofmeister | |
| 6,394,998 B1 | 5/2002 | Wallace et al. | |
| 6,817,974 B2 | 11/2004 | Cooper et al. | |
| 7,048,745 B2 | 5/2006 | Tierney et al. | |
| 7,316,681 B2 | 1/2008 | Madhani et al. | |
| 7,331,967 B2 | 2/2008 | Lee et al. | |
| 7,699,855 B2 | 4/2010 | Anderson et al. | |
| 7,727,244 B2 | 6/2010 | Orban, III | |
| 7,886,743 B2 | 2/2011 | Cooper et al. | |
| 7,947,050 B2 | 5/2011 | Lee et al. | |
| 7,947,051 B2 | 5/2011 | Lee et al. | |
| 8,333,755 B2 | 12/2012 | Cooper et al. | |
| 8,551,115 B2 * | 10/2013 | Steger et al. | 606/130 |
| 8,644,988 B2 * | 2/2014 | Prisco et al. | 700/245 |
| 2002/0087048 A1 | 7/2002 | Brock et al. | |
| 2004/0035243 A1 | 2/2004 | Duval | |
| 2005/0277875 A1 | 12/2005 | Selkee | |
| 2006/0235436 A1 * | 10/2006 | Anderson et al. | 606/130 |
| 2007/0156019 A1 | 7/2007 | Larkin et al. | |
| 2007/0232858 A1 * | 10/2007 | Macnamara et al. | 600/149 |
| 2007/0287992 A1 | 12/2007 | Diolaiti et al. | |
| 2008/0046122 A1 | 2/2008 | Manzo et al. | |
| 2008/0065102 A1 | 3/2008 | Cooper | |
| 2008/0087871 A1 * | 4/2008 | Schena | 254/226 |
| 2008/0103491 A1 | 5/2008 | Omori et al. | |
| 2009/0062813 A1 * | 3/2009 | Prisco et al. | 606/130 |
| 2009/0088774 A1 * | 4/2009 | Swarup et al. | 606/130 |
| 2010/0082041 A1 * | 4/2010 | Prisco | 606/130 |
| 2010/0170519 A1 * | 7/2010 | Romo et al. | 128/852 |
| 2010/0318101 A1 * | 12/2010 | Choi | 606/130 |
| 2011/0015650 A1 | 1/2011 | Choi et al. | |
| 2011/0213383 A1 | 9/2011 | Lee et al. | |
| 2011/0282359 A1 * | 11/2011 | Duval | 606/130 |
| 2011/0282491 A1 | 11/2011 | Prisco et al. | |
| 2012/0123441 A1 | 5/2012 | Au et al. | |
| 2012/0289974 A1 * | 11/2012 | Rogers et al. | 606/130 |

FOREIGN PATENT DOCUMENTS

| | | |
|---|---|---|
| JP | H06114000 A | 4/1994 |
| JP | H10249777 A | 9/1998 |
| JP | 2002200091 A | 7/2002 |
| JP | 2003024336 A | 1/2003 |
| JP | 2005288590 A | 10/2005 |
| JP | 2006061364 A | 3/2006 |
| JP | 2008104854 A | 5/2008 |
| JP | 2012504016 A | 2/2012 |
| WO | WO-2007136783 A2 | 11/2007 |
| WO | WO-2010039387 A1 | 4/2010 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Office Action mailed Dec. 26, 2014 for Japanese Application No. 20140021913 filed Feb. 7, 2008, 10 pages.

PCT/US09/55727 International Search Report and Written Opinion of the International Searching Authority, mailed Feb. 3, 2010, 9 pages.

Office Action mailed Sep. 30, 2015 for Japanese Application No. 20140021913 filed Feb. 7, 2008, 7 pages.

* cited by examiner

INSTRUMENT INTERFACE

CROSS-REFERENCE TO RELATED APPLICATIONS

This patent document is a continuation-in-part and claims the priority of U.S. patent application Ser. No. 12/286,644, filed Sep. 30, 2008 and also claims benefit of the earlier filing date of U.S. Provisional Pat. App. No. 61/485,702, filed May 13, 2011.

BACKGROUND

Robotically controlled systems such as employed for minimally invasive medical procedures can include large and complex equipment to precisely control and drive relatively small tools or instruments. (As used herein, the terms "robot" or "robotically" and the like include teleoperation or telerobotic aspects.) FIG. 1A illustrates an example of a known robotically controlled system 100. System 100, which may, for example, be part of a da Vinci® Surgical System available from Intuitive Surgical, Inc., includes a patient-side cart 110 having multiple arms 130. Each arm 130 has a docking port 140 that generally includes a drive system with a mechanical interface for mounting and providing mechanical power for operation of an instrument 150. Arms 130 can be used during a medical procedure to move and position respective medical instruments 150 for the procedure.

FIG. 1B shows a bottom view of a known instrument 150. Instrument 150 generally includes a transmission or backend mechanism 152, a main tube 154 extending from the backend mechanism 152, and a functional tip 156 at the distal end of the main tube 154. Tip 156 generally includes a medical tool such as a scalpel, scissors, forceps, or a cauterizing instrument that can be used during a medical procedure. Drive cables or tendons 155 connect to tip 156 and extend through main tube 154 to backend mechanism 152. Backend mechanism 152 typically provides a mechanical coupling between the drive tendons of the instrument 150 and motorized axes of the mechanical interface of a drive system 140. In particular, gears or disks 153 having features such as projections or holes that are positioned, sized, and shaped to engage complementary features on the mechanical interface of a drive system 140. In a typical instrument, rotation of disks 153 pulls on respective tendons 155 and actuates corresponding mechanical links in tip 156. System 100 can thus control movement and tension in drive tendons 155 as needed to position, orient, and operate tip 156. Further details of known surgical systems are described, for example, in U.S. Pat. No. 7,048,745 to Tierney et al., entitled "Surgical Robotic Tools, Data Architecture, and Use," which is hereby incorporated by reference in its entirety.

Instruments 150 of system 100 can be interchanged by removing one instrument 150 from a drive system 140 and then installing another instrument 150 in place of the instrument removed. The installation process in general requires that the features on disks 153 properly engage complementary features of the drive system 140. However, before installation, the orientations of disks 153 on instrument 150 are generally unknown to patient-side cart 110. Further, equipment such patient-side cart 110 is often covered for a medical procedure by a sterile barrier because of the difficulty in cleaning and sterilizing complex equipment between medical procedures. These sterile barriers can include a sterile adaptor (not shown) that is interposed between docking port 140 and instrument backend 152. For example, above referenced U.S. Pat. No. 7,048,745 and U.S. Pat. No. 7,699,855 to Anderson et al., entitled "Sterile Surgical Adaptor", which is hereby incorporated by reference in its entirety, describe some exemplary sterile barrier and adaptor systems.

A typical installation process for an instrument 150 involves mounting backend mechanism 152 without regard for the orientations of disks 153 on a drive system 140, possibly with an intervening sterile adaptor. The drive motors in drive system 140 may be then be rotated back and forth multiple times during the installation procedure to ensure that the complementary features mesh with and securely engage each other for operation of the newly installed instrument 150. At some point during the installation process, the drive motors become securely engaged to rotate respective disks 153. However, the instrument 150 being installed may move in an unpredictable manner at times during the installation procedure because the drive motors positively engage respective disks 153 of instrument 150 at different and unpredictable times. Such unpredictable motion is unacceptable when an instrument is inserted in a patient. In general, clear space is required around an instrument 150 to accommodate random movements of the instrument tip during an installation procedure.

SUMMARY

In accordance with an aspect of the invention, a mechanical interface for a robotic medical instrument permits engagement of the instrument and a drive system without causing movement of the tip of the instrument. Accordingly, an instrument can be engaged with the drive system in a patient-side cart after the instrument is manually posed in a desired configuration or even after the instrument has been inserted for a medical procedure. This permits manual insertion of an instrument followed by robotic control of the instrument.

In one embodiment, an instrument interface includes a symmetrical, tapered or cylindrical projection on one of a medical instrument and a drive system (potentially including a sterile barrier) and a complementary bore in the other of the drive system or the instrument. With cylindrical projection and bore, the diameter of the bore can contract, for example, using the tension in a tendon wrapped around the mechanical element containing the bore, to reduce the diameter of the bore and provide the instrument with frictional forces sufficient to transmit driving torque to the medical instrument. In any case, symmetry of the projection and the bore allows the projection to be compression fit into the bore regardless of the rotation angle of the drive system relative to the instrument.

In one specific embodiment of the invention, a system includes a medical instrument and a drive system. The medical instrument includes a rotatable element that when rotated actuates the medical instrument. The drive system has an interface configured to releasably engage the medical instrument, and a first feature of the rotatable element and a second feature of the interface are shaped to engage each other without inducing rotation that actuates the medical instrument.

Another embodiment of the invention is a medical instrument. The medical instrument includes an actuated structure and a mechanical element connected so that rotation of the mechanical element actuates the actuated structure. The mechanical element has an engagement feature shaped such that for any pose of the actuated structure, the engagement feature can engage a complementary engagement feature on a drive system without inducing rotation that actuates the actuated structure.

Yet another embodiment of the invention is a drive system for a medical instrument. The drive system includes a motor; and an interface coupled to the motor and configured to releasably engage the medical instrument so that rotation of the motor actuates the medical instrument. The interface includes an engagement feature shaped such that for any pose of the medical instrument, the engagement feature can engage a complementary engagement feature of the medical instrument without inducing rotation that actuates the medical instrument.

Still another embodiment of the invention is a method for engaging a medical instrument and a drive system. The method includes bringing a first feature on a rotatable element of the medical instrument into contact with a second feature on a drive element of the drive system without rotating either of the elements. An engagement force is then applied to create friction between the rotatable element and the drive element without rotating either of the elements. When thus engaged, the drive system can be operated to actuate the medical instrument, and the friction transfers torque that the drive system applies to the first rotatable element to the second rotatable element and thereby actuates the mechanical instrument.

BRIEF DESCRIPTION OF THE DRAWINGS

Use of the same reference symbols in different figures indicates similar or identical items.

DETAILED DESCRIPTION

In accordance with an aspect of the invention, a medical instrument can be installed on and engaged with a drive system without actuating or otherwise moving the joints or tip of the instrument. Engagement without actuation can be implemented using symmetric mechanical elements that securely engage through compression or friction to maintain the relative orientation of a drive mechanism and the mechanical interface of the instrument. In one embodiment, a symmetric tapered shaft of a drive system or a backend mechanism fits into a symmetric tapered bore or slot in a mechanical element of the backend mechanism or drive system, and friction maintains the orientation of the shaft and the slotted mechanical element. In another specific embodiment, a symmetric shaft can be inserted into a mechanical element containing a bore that contracts in diameter to securely hold the relative orientation of the shaft and the mechanical element. For example, a shaft of a drive motor can fit into a bore within a capstan that is sufficiently flexible that tension in a tendon wrapped around the capstan causes the bore to collapse onto the shaft. The ability to install an instrument without actuating the instrument allows posing of the instrument in a desired configuration before the instrument is installed on a drive system and allows installation of an instrument after the instrument has been inserted into a cannula or even into a patient.

Figure 1A:
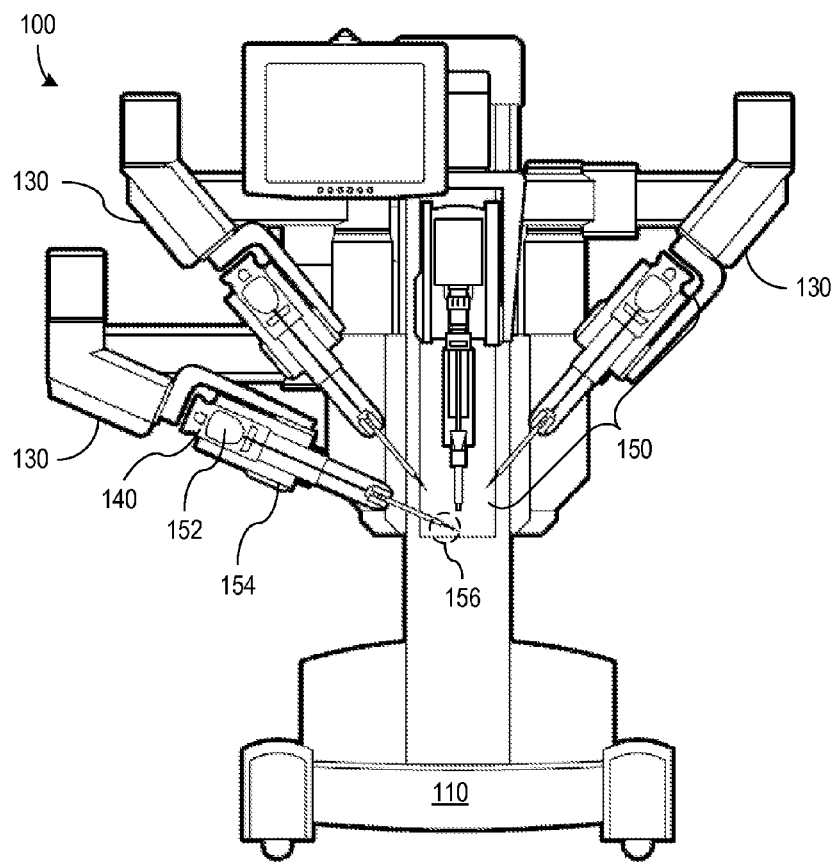
FIG. 1A shows a patient-side cart of a robotically controlled system that may employ a medical instrument in accordance with an embodiment of the invention.
Figure 1B:
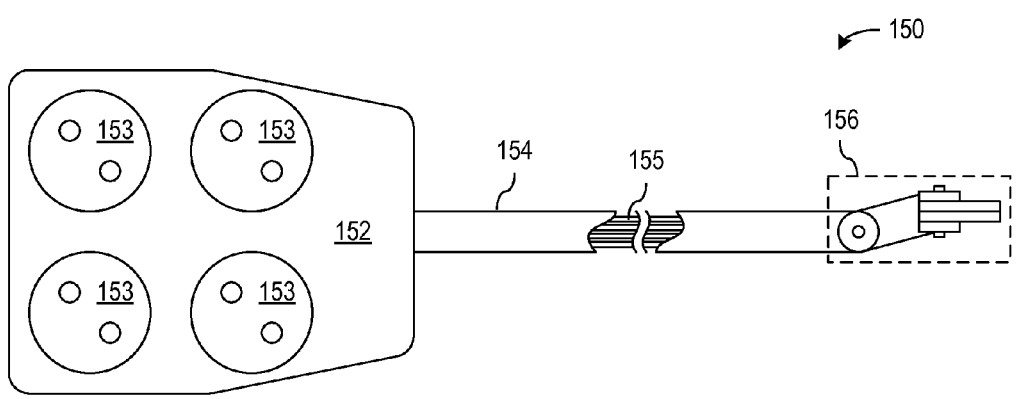
FIG. 1B shows a bottom view of a known medical instrument employing drive gears or disks that require rotation for alignment with a drive motor.
Figure 2:
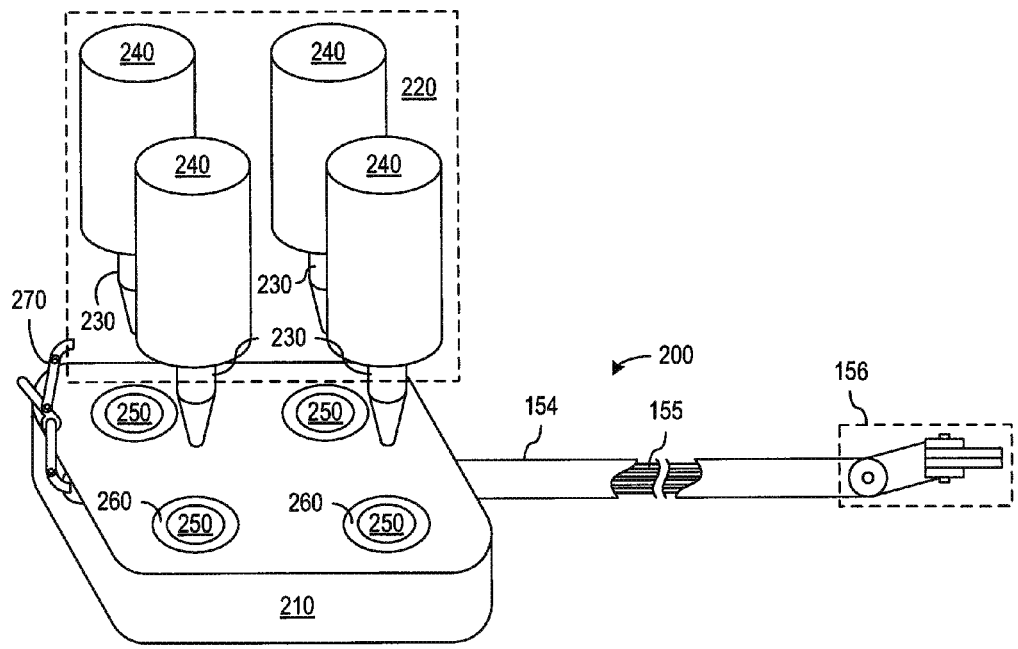
FIG. 2 shows an embodiment of the invention in which an instrument can engage a set of drive motors without movement or actuation of the working tip of the instrument.

FIG. 2 illustrates an embodiment of the invention in which a medical instrument 200 has a backend mechanism 210 that mounts on a drive system 220 having one or more tapered drive shafts 230. Drive system 220 may be part of a docking port or a tool holder of a medical system such as the patient-side cart 110 of FIG. 1, which allows instrument 200 to be installed or removed for different medical procedures or during a medical procedure. Tapered shafts 230 can be the shafts of drive motors 240 of drive system 220 or can be separate elements that attach to the motor shafts and transmit motor rotation to backend mechanism 210 for movement of a jointed section of instrument 200, e.g., an instrument tip 156. In general, instrument tip 156 can be of any desired type but is illustrated in FIG. 2 as being on the distal end of a main shaft 154 through which tendons 155 extend and connect to tip 156. Backend mechanism 210 generally contains a transmission mechanism (not shown) that converts the rotation of motors 240 into movement of tendons 155 which operate the joints of instrument 200 including joints in tip 156.

Tapered shafts 230 can be simple, low cost, and robust mechanical elements that are precisely machined using conventional techniques to produce a tapered shape with a circular cross-section. Many types of tapers could be employed on tapered shafts 230. For example, Morse tapers with or without an end tang or guide could be used. Tapered shafts 230 are free to spin on their axis and are symmetric about their respective rotation axes, i.e., have circular cross-sections.

Figure 3:
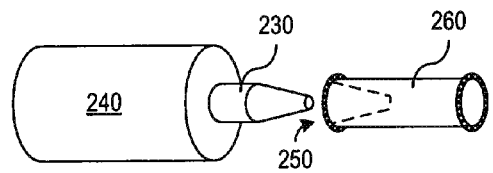
FIG. 3 shows a drive motor and a mechanical element of a backend mechanism in accordance with an embodiment of the invention in which the drive motor can engage the backend mechanism without turning of the mechanical element.

Each tapered shaft 220 is further shaped to fit into a complementary tapered hole 250 or slot in a mechanical element 260 of backend mechanism 210. Mechanical element 260 may be, for example, a hollowed-out spindle having a tapered hole 250 that matches the shape of the corresponding tapered shaft 230 and in particular has circular cross-sections matching those of tapered shafts 220. More generally, tapered holes 250 can be formed in any mechanical elements 260 of instrument backend 210 that are free to spin on their axis, where a mechanical transmission system of backend mechanism 210 converts the rotations of the slotted mechanical elements 260 into movements of tendons 155 and instrument tip 156. For example, FIG. 3 shows how a tapered shaft 230 of a motor 240 directly fits into a tapered hole or bore 250 in a capstan 260. In one specific embodiment, tapered holes 250 are formed in capstans that transmit the motion to tendons 155 as described in U.S. Pat. App. Pub. No. 2010/0082041, entitled "Passive Preload and Capstan Drive for Surgical Instruments," which is hereby incorporated by reference in its entirety. More generally, a capstan is just one example of a mechanical element 260 that may be employed within backend mechanism 210 to convert motor rotation into tendon movement and instrument actuation.

Figure 4:
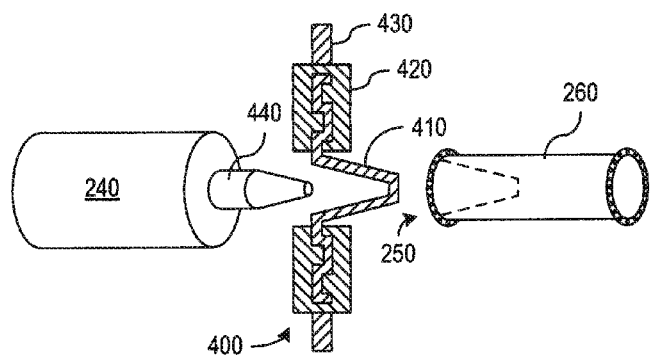
FIG. 4 illustrates an embodiment of the invention in which a portion of a sterile adaptor is interposed between a drive motor and a mechanical element of the backend mechanism of a medical instrument.

FIG. 4 schematically illustrates how a sterile adaptor 400 in a sterile barrier can be interposed between a drive element 440 and a mechanical element 260 that is rotatable to actuate a medical instrument. In the illustrated configuration, sterile adaptor 400 includes an element 410 that is free to rotate in a circumferential bearing 420 that maintains a sterile barrier by means of a labyrinth seal that performs the desired medical function while allowing element 410 to rotate about an axis corresponding to the rotation axis of drive element 440 and rotatable element 260. Element 410 may be, for example, of a layer of a mechanically resistant plastic about 0.5 to 2 mm thick that is molded to be interposed between drive element 440 and a hole 250 in rotatable element 260. In particular, element 410 in FIG. 4 is shaped to receive drive element 440 on the manipulator side and to have a projection that fits into tapered hole 250 in rotatable element 260 that is part of the backend mechanism of a medical instrument. A sterile sheet 430 or other portions of the sterile barrier can be connected to bearing 420 to maintain surgical field sterility. FIG. 4 illustrates features of a sterile adaptor in a schematic fashion to illustrate general working principles relevant to the present invention, U.S. Pat. Nos. 7,048,745 and 7,699,855, which are incorporated by reference above, provide additional description of the features of some sterile adaptors for medical instruments.

FIG. 4 also shows an embodiment of the invention in which drive element 440 has a tapered shape that can engage barrier element 410 without rotation. Alternatively, drive element 440 could have a keyed or rough surface, and barrier element could be smooth but sufficiently compliant to be forced onto drive element 440. In yet another alternative embodiment, drive element 440 has a keyed engagement feature with projections or indentations that engage complementary features of barrier element 410. With keyed features on drive element 440 and the manipulator side of barrier element 410, rotation of drive element 440 or barrier element 410 may be necessary in order to align the keyed features when the sterile barrier is fitted to a manipulator. However, the sterile barrier can be fitted to the manipulator once for a medical procedure and is fitted before any medical instruments are engaged on the manipulator. Rotation of drive element 440, barrier element 410, or rotatable element 260 is not required when engaging an instrument on the drive system because the instrument side of barrier element 410 has a surface shaped to fit bore 250 without any rotation.

Instrument engagement using the system of FIG. 2 can be performed by slipping the holes 240 in instrument backend 210 onto tapered shafts 230 of docking port 220, with or without an interposed sterile adapter. A latch or other mechanism 270 can be used to provide an engagement force that presses backend mechanism 210 onto docking port 220 and drives tapered shafts 230 into tapered holes 250. The shapes of shafts 230 and holes 250 automatically accommodate some initial misalignment between instrument 200 and drive system 220 since the tapers guide shafts 230 and holes 250 into the desired relative positions. Additional misalignment between backend mechanism 210 and docking port 220 or relative misalignment or spacing variation of the drive axes of backend mechanism 210 or docking port 220 can be accommodated using flexible mountings for tapered shafts 230 or slotted elements 260 as described further below. When engaged and held in place, compression and the friction across the entire surface of each tapered shaft 230 contacting the matching inner surface of a corresponding hole 240 can provide a large amount of torque transmission, so that keys or gear teeth are not required to transfer torque or rotational movement from drive system 220 to backend mechanism 210. Further, no rotation of motors 240 or slotted mechanical elements 260 of backend mechanism 210 is required during the engagement procedure. Also, the instrument can be engaged while having any desired configuration of slotted elements 260 and any pose of tip 156, and instrument tip 156 does not move during engagement. The lack of tip movement makes the engagement process possible while tip 156 is inserted in a cannula or even at an operating site within a patient.

Control of medical instrument 200 after engagement of backend mechanism 210 and drive system 220 can be based on a measurement of the pose (e.g., the positions of joints) of medical instrument 210 and measurements of the rotation angles of each of motors 240. Alternatively, a control process using differences between measured and desired instrument pose or configuration could be employed. U.S. patent application Ser. No. 12/945,734, entitled, "Tension Control in Actuation of Multi-Joint Medical Instruments" and U.S. patent application Ser. No. 12/780,417, entitled "Drive Force Control in Medical Instrument Providing Position Measurements" describe exemplary systems for control of medical instruments and are hereby incorporated by reference in their entirety.

Figure 5:
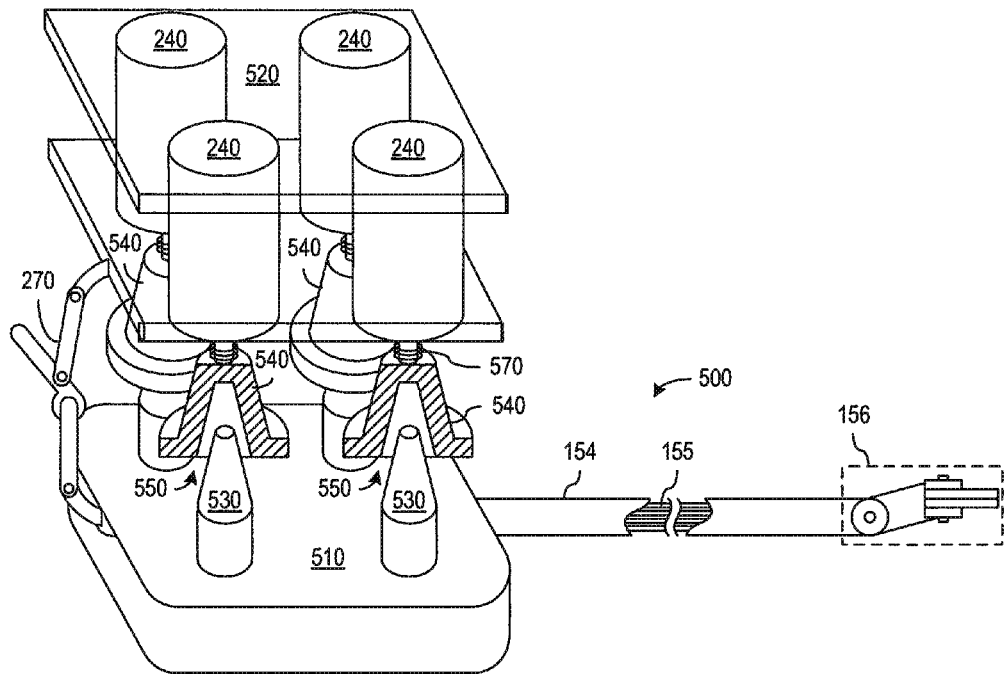
FIG. 5 shows an embodiment of the invention in which a medical instrument has tapered projections that can engage drive motors without movement or actuation of the tip of the medical instrument.

FIG. 2 illustrates a system in which drive system 220 includes one or more tapered shafts 230 and instrument backend 210 includes complementary tapered holes 230. FIG. 5 illustrates a system in accordance with an alternative embodiment in which tapered shafts 530 extend from a backend mechanism 510 of a medical instrument 500 and are rotated to operate the transmission within backend mechanism 510 and actuate or move joints of instrument 500. In this configuration, motors 240 in a drive system 520 have shafts with fixtures 540 shaped to provide tapered holes 550 that are complementary to the shape of tapered shafts 530 or an interposed portion of a sterile adaptor. Other than the reversing of the positions of the tapered shafts and the tapered holes, backend mechanism 510 and instrument holder 520 of system 500 can be engaged and operated in the same manner as backend mechanism 210 and instrument holder 220 of system 200, which is described above with reference to FIG. 2. As described above, a docking system can attach medical instrument 500 to drive system 520 and apply an engagement force so that the friction between features 530 and 540 is sufficient to transmit the torque required for operation of medical instrument 500. The docking system could include, for example, a latch 270 and a spring preload 570.

Figure 6:
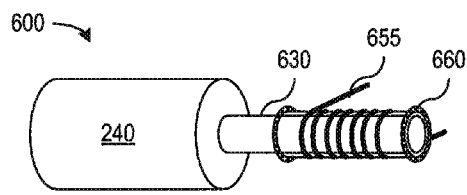
FIG. 6 shows an embodiment of the invention that uses compression caused by a tendon wrapped around a capstan to contract a bore in the capstan and engage a drive motor.

In accordance with another aspect of the invention, a motor in a drive system can operate a mechanical element of a backend mechanism through a frictional engagement created by radial compression of a hole or bore in a mechanical element. FIG. 6, for example, illustrates a system 600 including a motor 240 having a cylindrical shaft 630 that fits within a cylindrical bore in a mechanical element 660 of a backend mechanism such as backend mechanism 210 of FIG. 2. Mechanical element 660 is a capstan, and a drive tendon 655, which may attach to an articulated joint of the instrument, is wound around capstan 660. Tendon 655 can be a cable, a wire, a filament, or similar structure that is able to wrap around capstan 660 and may be made of metal or a synthetic material. Capstan 660 is radially flexible so that the application of tension in tendon 655 causes the diameter of the bore in capstan 660 to decrease, thereby clamping capstan 660 onto shaft 630 with or without an intervening, substantially cylindrical plastic component of a sterile barrier (not shown). One more surface of the sterile barrier component, capstan 660, or shaft 630 may include splines, teeth, or other features to improve the traction and torque transmission capability of the engagement, provided that the other surface of the sterile adaptor can engage the contoured surface without rotation.

However, meshing of the splines or teeth of two surfaces generally requires rotation of shaft 630 and capstan 660, which may be undesirable.

The process of engaging the instrument on a drive system including motor 240 may further begin with tendon 655 being sufficiently relaxed so that shaft 630 (with or without an interposed portion of a sterile barrier) can slide into the bore of mechanical element 660, without any rotation of mechanical element 660. Shaft 630 and the bore of mechanical element 660 can be symmetrical (e.g., have a circular cross-section) so that shaft 630 can be inserted into mechanical element 660 regardless of the relative orientation of shaft 630 and mechanical element 660. A mechanism within the backend mechanism can then increase or apply the pre-tension to tendon 655 to cause the wraps of tendon 655 to clamp flexible mechanical element 660 on shaft 630. For example, displacing a capstan in a proximal direction relative to the body of an instrument can increase the tension in both ends of a tendon extending from the capstan, causing opposing torques on a joint coupled to the ends of tendon 655. As a result, no joint movement occurs when the tension is increased. Alternatively, when only one end of tendon 655 attaches to an articulated joint, pre-tension in tendon 655 can be preset to permit insertion of shaft 630 (with at least one smooth, cylindrical interface between the capstan, sterile barrier, and input shaft) into capstan 660, so that capstan 660 couples more strongly to shaft 630 when driven in a direction that increases tension in tendon 655. Capstan 660 may then be permitted to slip relative to shaft 630 when driven in the reverse direction.

Figure 7:
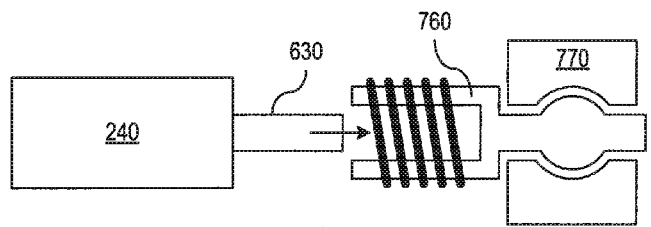
FIG. 7 illustrates an embodiment of the invention employing a floating or loose shaft to accommodate misalignment between a drive mechanism and a medical instrument.
Figure 8:
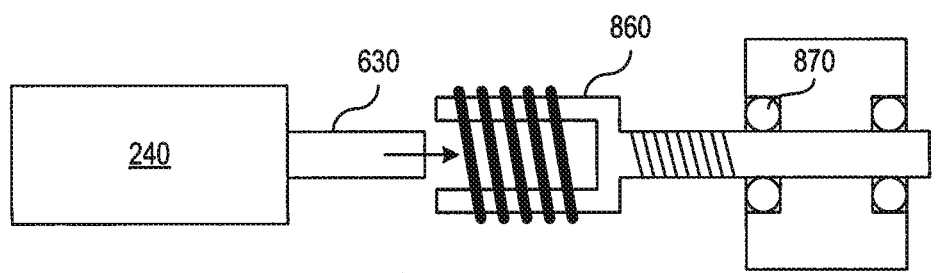
FIG. 8 illustrates an embodiment of the invention employing a flexible shaft to accommodate misalignment between a drive mechanism and a medical instrument.

Motor shaft 630 and the bore of mechanical element 660 do not have tapering that accommodates misalignment in the same manner as embodiments of the invention using tapered shafts and holes. However, compliance can be provided in shaft 630 or capstan 660 to accommodate initial misalignment of motor 240 and capstan 660 during an engagement process. FIG. 7, for example, shows an embodiment of the invention in which a capstan 760 is loosely retained in a structure 770 of the backend mechanism in such a way that capstan 760 can move into alignment with shaft 530 and then be supported primarily by shaft 630 and the bearings of motor 240 when capstan 760 is engaged with motor 630. Alternatively, as shown in FIG. 8, a capstan 860 may be supported by bearings 870 in the backend mechanism of an instrument but incorporate a flexure, e.g., a spring or helical structure, to allow movement for alignment of shaft 630 and capstan 860. The compliance of the mountings shown in FIGS. 7 and 8 can accommodate misalignment of a drive element in a drive system and a corresponding rotatable element in a medical instrument and accommodate differences in the spacing or orientation of multiple drive elements in a drive system relative to the corresponding rotatable elements in a medical instrument.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A system comprising:
 a medical instrument that includes a rotatable element having a first feature, wherein rotation of the rotatable element actuates the medical instrument; and
 a drive system having an interface configured to releasably engage the medical instrument, wherein the interface includes a drive element with a second feature, and the first and second features are shaped such that for any rotation angle of the rotatable element relative to the drive element, the first and the second features engage each other without inducing rotation that actuates the medical instrument.

2. The system of claim 1, wherein for any pose of the medical instrument, the first and the second features engage each other without rotation.

3. The system of claim 1, wherein friction between the first feature and the second feature permits the drive system to rotate the rotatable element to actuate the medical instrument.

4. The system of claim 1, further comprising a sensor configured to measure a pose of the medical instrument upon engagement of the medical instrument and the drive system.

5. The system of claim 1, wherein each of the first and the second features has a circular cross-section.

6. The system of claim 5, wherein one of the first and second features comprises a tapered projection and the other of the first and second features comprise a tapered hole in which the tapered projection fits.

7. The system of claim 1, wherein one of the first and second features comprises a cylindrical projection and the other of the first and second features comprises a cylindrical bore.

8. The system of claim 7, wherein the feature including the cylindrical bore is compressible to create friction between the first and second features that permits the drive system to rotate the rotatable element to actuate the medical instrument.

9. The system of claim 1, further comprising a flexible mounting on which one of the first and second features is mounted, wherein the flexible mounting provides compliance that accommodates misalignment of the first and second features during engagement of the medical instrument on the drive system.

10. The system of claim 9, wherein the flexible mounting comprises a floating bearing.

11. The system of claim 9, wherein the flexible mounting comprises a flexible shaft.

12. The system of claim 1, wherein:
 the rotatable element comprises a capstan around which a tendon is wrapped;
 the first feature comprises a bore within the capstan;
 the second feature fits within the bore; and
 the capstan is flexible so that the bore has a diameter that changes with tension in the tendon.

13. The system of claim 1, wherein:
 the medical instrument includes a plurality of rotatable elements having respective first features, wherein rotations of the rotatable elements actuate the medical instrument; and
 the interface includes a plurality of drive elements having respective second features, wherein the second features are shaped to engage corresponding first features without inducing rotation that actuates the medical instrument.

14. The system of claim 13, wherein at least one of the drive elements and the rotatable elements have flexible mountings configured to provide compliance sufficient to accommodate expected misalignment of the drive system and the medical instrument during engagement of the medical instrument on the drive system and accommodate relative misalignment between axes of the drive elements and axes of the rotatable elements.

15. The system of claim 1, wherein the drive system further comprises a sterile barrier including an adaptor, and the second feature is formed on a surface of the adaptor.

16. A medical instrument comprising:
 an actuated structure; and a rotatable element connected to the actuated structure so that rotation of the rotatable element actuates the actuated structure, the rotatable element having an engagement feature shaped such that for any rotation angle of the rotatable element relative to a complementary engagement feature on a drive system, the engagement feature engages the complementary engagement feature without inducing rotation that actuates the actuated structure.

17. The instrument of claim 16, wherein the engagement feature has a circular cross-section positioned to engage a corresponding circular cross-section of the complementary engagement feature.

18. The instrument of claim 17, wherein the engagement feature comprises one of a tapered projection, a tapered hole, a cylindrical projection, and a cylindrical bore.

19. The instrument of claim 16, wherein:
the rotatable element comprises a capstan around which a tendon is wrapped;
the engagement feature comprises a bore within the capstan; and
the capstan is flexible so that a diameter of the bore changes with tension in the tendon.

20. The instrument of claim 16, further comprising a flexible mounting on which the rotatable element is mounted, wherein the flexible mounting provides compliance that accommodates misalignment of the medical instrument during engagement of the medical instrument on the drive system.

21. The instrument of claim 20, wherein the flexible mounting comprises a floating bearing.

22. The instrument of claim 20, wherein the flexible mounting comprises a flexible shaft.

23. The instrument of claim 16, further comprising a plurality of rotatable elements having respective engagement features shaped such that for any pose of the actuated structure, the engagement features engage complementary engagement features on the drive system without inducing rotation that actuates the actuated structure.

24. The instrument of claim 23, further comprising flexible mountings respectively coupled to the rotatable elements, wherein the flexible mountings are configured to provide compliance sufficient to accommodate expected misalignment of the drive system and the medical instrument during engagement of the medical instrument on the drive system and accommodate relative misalignment between axes of the rotatable elements and respective axes of drive elements in the drive system.

25. A drive system for a medical instrument comprising:
a motor; and
an interface that is coupled to the motor and configured to releasably engage a first feature on a rotatable element of the medical instrument, wherein when the interface is engaged with the medical instrument, rotation of the motor rotates the first feature and actuates the medical instrument, the interface including a drive element with a second feature shaped such that for any rotation angle of the first feature relative to the drive element, the first and second features operationally engage each other without inducing rotation that actuates the medical instrument.

26. The system of claim 25, wherein the second feature has a circular cross-section positioned to engage a corresponding circular cross-section of the first feature.

27. The system of claim 25, further comprising a plurality of drive elements having respective engagement features shaped such that for any pose of the medical instrument, the engagement features engage complementary engagement features on the medical instrument without inducing rotation that actuates the medical instrument.

28. The system of claim 27, further comprising flexible mountings respectively coupled to the drive elements, wherein the flexible mountings are configured to provide compliance sufficient to accommodate expected misalignment of the drive system and the medical instrument during engagement of the medical instrument on the drive system and accommodate relative misalignment between axes of the drive elements and respective axes of rotatable elements in the drive system.

29. The system of claim 25, further comprising a sterile barrier including an adaptor that forms part of the drive element, where the second feature is formed on a surface of the adaptor.

30. A drive system for a medical instrument, comprising:
a motor; and
an interface that is coupled to the motor and configured to releasably engage the medical instrument so that when the interface engages the medical instrument, rotation of the motor actuates the medical instrument, the interface including a drive element with an engagement feature shaped such that for any pose of the medical instrument, the engagement feature engages a complementary engagement feature of the medical instrument without inducing rotation that actuates the medical instrument, wherein
the engagement feature has a circular cross-section positioned to engage a corresponding circular cross-section of the complementary engagement feature, and wherein
the engagement feature comprises one of a tapered projection, a tapered hole, a cylindrical projection, and a cylindrical bore.

31. A drive system for a medical instrument, comprising:
a motor;
an interface that is coupled to the motor and configured to releasably engage the medical instrument so that when the interface engages the medical instrument, rotation of the motor actuates the medical instrument, the interface including a drive element with an engagement feature shaped such that for any pose of the medical instrument, the engagement feature engages a complementary engagement feature of the medical instrument without inducing rotation that actuates the medical instrument; and
a flexible mounting on which the engagement feature is mounted, wherein the flexible mounting provides compliance that accommodates misalignment of the drive system during engagement of the medical instrument on the drive system.

32. The system of claim 31, wherein the flexible mounting comprises a floating bearing.

33. The system of claim 31, wherein the flexible mounting comprises a flexible shaft.

* * * * *